United States Patent
Sparks et al.

(10) Patent No.: US 7,879,241 B2
(45) Date of Patent: Feb. 1, 2011

(54) METHOD OF TREATING A BODILY FLUID

(75) Inventors: Douglas Ray Sparks, Whitmore Lake, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 318 days.

(21) Appl. No.: 12/106,642

(22) Filed: Apr. 21, 2008

(65) Prior Publication Data

US 2008/0214978 A1    Sep. 4, 2008

Related U.S. Application Data

(62) Division of application No. 11/160,403, filed on Jun. 22, 2005, now abandoned.

(60) Provisional application No. 60/582,976, filed on Jun. 28, 2004.

(51) Int. Cl.
*B01D 61/24* (2006.01)
*B01D 61/28* (2006.01)

(52) U.S. Cl. .............. 210/646; 210/321.71; 604/5.01; 604/6.09

(58) Field of Classification Search .......... None
See application file for complete search history.

(56) References Cited

U.S. PATENT DOCUMENTS

| | | | | |
|---|---|---|---|---|
| 5,237,993 A * | 8/1993 | Skrabal | | 600/309 |
| 6,477,901 B1 * | 11/2002 | Tadigadapa et al. | | 73/861.352 |
| 7,131,956 B1 * | 11/2006 | Pirazzoli et al. | | 604/6.09 |
| 2002/0009385 A1 * | 1/2002 | Krivitski et al. | | 422/44 |
| 2002/0023880 A1 * | 2/2002 | Pedrini et al. | | 210/646 |
| 2002/0194908 A1 * | 12/2002 | Sparks | | 73/204.26 |
| 2005/0085760 A1 * | 4/2005 | Ware et al. | | 604/4.01 |

* cited by examiner

*Primary Examiner*—Krishnan S Menon
(74) *Attorney, Agent, or Firm*—Hartman & Hartman, P.C.; Gary M. Hartman; Domenica N. S. Hartman

(57) ABSTRACT

A method of treating a bodily fluid withdrawn and then returned to a living body. The method involves withdrawing the bodily fluid from the living body and causing the bodily fluid to flow through a treatment system, altering at least the density of the bodily fluid through the action of a second fluid as the bodily fluid flows through the treatment system, sensing at least the density and flow rate of the bodily fluid before the density thereof is altered by the second fluid, sensing at least the density and flow rate of the bodily fluid after the density thereof is altered by the second fluid, sensing at least the density and flow rate of the second fluid, controlling the density and/or flow rate of the second fluid based on the sensed densities and flow rates, and returning the bodily fluid to the living body.

10 Claims, 3 Drawing Sheets

METHOD OF TREATING A BODILY FLUID

CROSS REFERENCE TO RELATED APPLICATIONS

This is a division patent application of U.S. patent application Ser. No. 11/160,403 filed Jun. 22, 2005 (now abandoned), which claims the benefit of U.S. Provisional Application No. 60/582,976, filed Jun. 28, 2004. The contents of these prior applications are incorporated herein by reference.

BACKGROUND OF THE INVENTION

The present invention generally relates to medical treatment systems that receive and return fluids to a patient. More particularly, this invention relates to a medical treatment system suitable for use in dialysis and other therapies in which a fluid is withdrawn and then returned to a living body, and flow rates, fluid concentrations, temperature, and other process parameters can be accurately sensed with flow rate sensors.

Hemodialysis and peritoneal dialysis are used to remove impurities from the blood, such as in the treatment of renal failure and various toxic conditions. In hemodialysis, a patient's blood is shunted from the body through a machine for diffusion and ultrafiltration before being returned to the patient's circulation system. Peritoneal dialysis requires access to the peritoneal cavity, and involves the use of a catheter to fill the peritoneal cavity with a dialysis solution. Waste products pass from the blood into the dialysis solution through the peritoneum, and are then removed from the peritoneal cavity when the dialysis solution is drained.

Traditional hemodialysis is performed by accessing the blood stream through an external shunt or arteriovenous fistula. The external shunt is constructed by inserting two cannulas through the skin into a large vein and artery. When performing dialysis the two cannulas are used separately, allowing arterial blood to flow to a dialyzer with which wastes (urea, creatinine, etc.) are removed with a dialysate solution, after which the dialyzed blood is returned to circulation through the cannula in the vein. A blood pump is used to maintain flow through the dialysis system, and various sensors are used to monitor the system, such as to monitor the rate of heparin (anticoagulant) infusion, the conductivity and temperature of the dialysate solution, and blood leak rates in the dialysate solution leaving the dialyzer. Pressure sensors, air bubble detectors, temperature monitors, leak detectors, and conductivity meters have all been used, each usually as a separate individual sensor that often must accommodate the relatively high blood flow rates that must be maintained within the system to avoid clotting. High dialysate flow rates through the dialyzer and the dialysis membrane are also desirable to maximize the removal rate of urea and other wastes. Consequently, accurate flow rate measurement is required, which in the past have included the use of ultrasonic flow sensors, optical sensors, and volumetric containers. Finally, additional sensors, equipment, and procedures have been used to monitor the efficiency and progress of dialysis procedures, such as the slow-flow method, saline-dilution method, blood temperature modules, monitoring urea and hematocrit levels, and the occlusion method.

It would be desirable to improve yet simplify accurate monitoring of dialysis treatments while avoiding clotting and other dialysis-related problems that can occur, including hemorrhaging, hypotension, infection, thrombophlebitis, etc.

BRIEF SUMMARY OF THE INVENTION

The present invention provides a method of treating a bodily fluid that has been withdrawn from a living body, and is subsequently returned to a living body.

The method involves withdrawing the bodily fluid from the living body and causing the bodily fluid to flow through a treatment system, altering at least the density of the bodily fluid through the action of a second fluid as the bodily fluid flows through the treatment system, sensing at least the density and flow rate of the bodily fluid before the density thereof is altered by the second fluid, sensing at least the density and flow rate of the bodily fluid after the density thereof is altered by the second fluid, sensing at least the density and flow rate of the second fluid, controlling the density and/or flow rate of the second fluid based on the sensed densities and flow rates, and returning the bodily fluid to the living body.

The treatment system utilized by the method preferably includes outgoing and incoming fluid lines connected to the living body for transporting the fluid from the living body, through the treatment system, and back to the living body, means for altering at least the density of the fluid as it flows through the system, and sensing units within the system and adapted to sense densities and flow rates of the fluids.

In the context of a dialysis treatment system, the method provides for the detection of additives (e.g., anticoagulants), wastes (e.g., urea and hematocrit), contaminants (e.g., sterilization fluids), and air bubbles in the blood based on density of the blood, sensing of the concentration of the dialysate used to cleanse the blood, detection of blood leakage through the dialyzer, and monitoring of the efficiency and progress of the dialysis procedure. Additional monitoring capabilities are achieved by including the capability to accurately sense flow rates and temperature, such as ensuring the proper flow rates, dosage rates, mixing, and temperatures of the various fluids, with the result that multiple functions are incorporated into a flow sensor capable of replacing a variety of sensors previously used in dialysis treatment systems, as well as other treatment systems and methods used in the medical field.

Other objects and advantages of this invention will be better appreciated from the following detailed description.

DETAILED DESCRIPTION OF THE INVENTION

Figure 1:
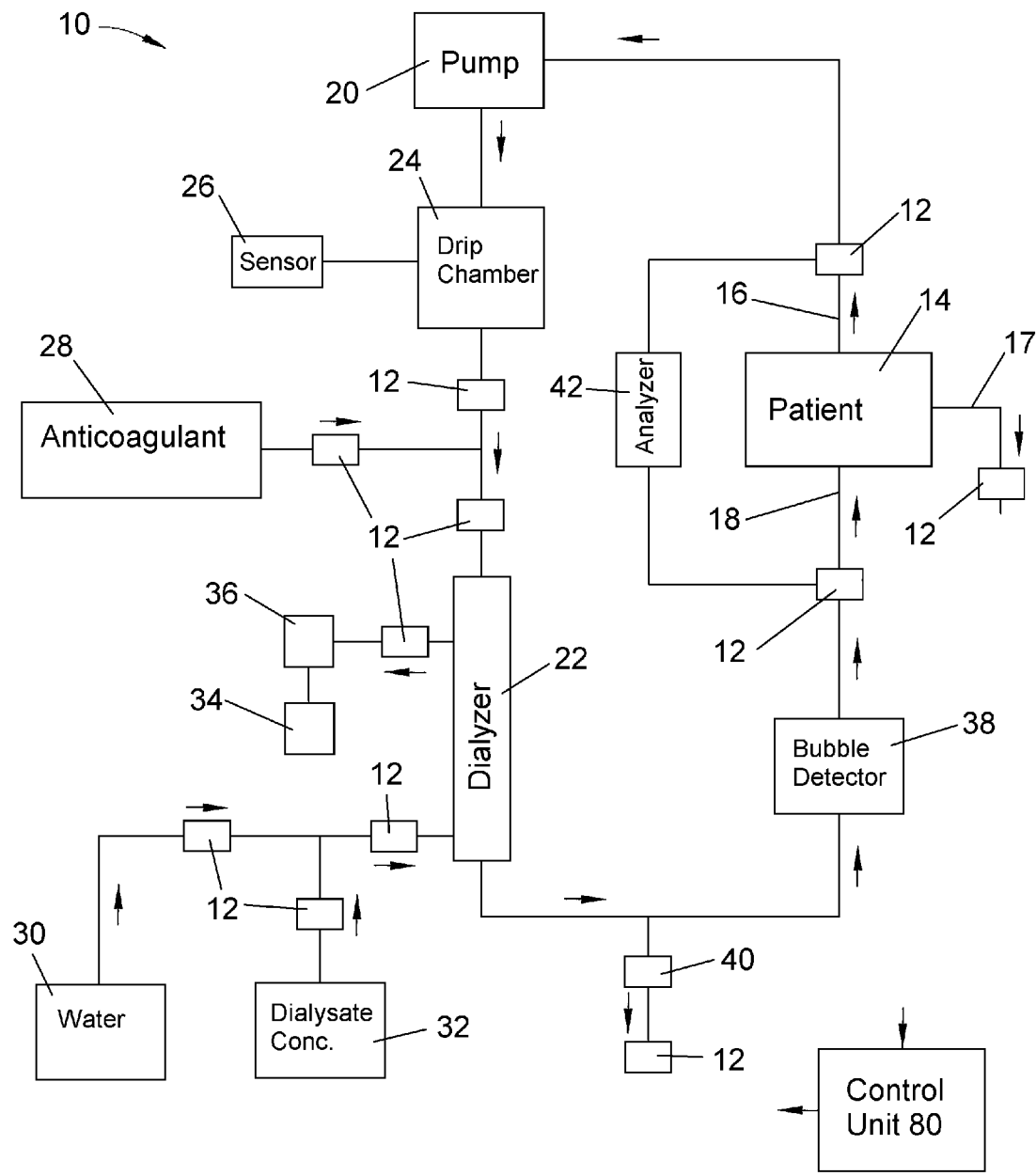
FIG. 1 is a schematic representation of a dialysis treatment system in accordance with an embodiment of this invention.

Illustrated in FIG. 1 is a dialysis treatment system 10 capable of making use of multiple sensing units 12 of a type or types in accordance with this invention. The system 10 is represented as being generally configured similar to traditional hemodialysis. The blood stream of a patient 14 is accessed through an external shunt or arteriovenous fistula, such as by inserting two cannulas (or cannulae) 16 and 18 through the skin into a large vein and artery. Arterial blood flows into the system 10 through the cannula 16 and is returned to the patient 14 through the cannula 18 in the vein.

The system 10 includes a blood pump 20 connected to a dialyzer 22 with which wastes (urea, creatinine, etc.) are removed from the blood with a dialysate solution. The blood pump 20 is necessary to maintain acceptable flow rate through the system 10 and particularly through the dialyzer 22 to avoid clotting. As is also generally conventional, the system 10 may include an arterial drip chamber 24 and arterial pressure monitor 26 between the pump 20 and dialyzer 22. An anticoagulant is infused into the blood flowing into the dialyzer 22 with an infusion pump 28. Before being introduced into the dialyzer 22, the dialysate solution is prepared by mixing purified water 30 and a dialysate concentrate 32 at a controlled rate. The dialysate solution is drawn from the dialyzer 22 with a pump 34 and monitored with a blood leak detector 36. Finally, an air bubble detector 38 is shown between the dialyzer 22 and venous cannula 18 to check for air bubbles in the blood that, if delivered to the patient's blood stream, can cause venous air embolisms that may lead to stroke or death.

While the invention will be described with reference to the hemodialysis treatment system 10 shown in FIG. 1, the invention is also applicable to other treatment systems in which a fluid is withdrawn and then returned to the human body, including but not limited to peritoneal dialysis, hemofiltration and assistance to the kidneys, lungs, liver and artificial organs.

According to a preferred aspect of the invention, each sensing unit 12 employs a sensor that can accurately measure density, and preferably also flow rate and optionally temperature of a fluid passing through it. More particularly, using the density output of the units 12, the chemical concentration of any fluid flowing in the system 10 (blood, dialysate, anticoagulant, water, dialysate solution, etc.) can be measured. For example, density output can be used to indicate the urea or hematocrit content within the blood before and after passing through the dialyzer 22 to monitor the effectiveness and progress of a dialysis treatment. Density output can also be utilized to monitor and control the mixing of the water 30 and dialysate concentrate 32 to make the dialysate solution, and to monitor and more accurately control the flow of anticoagulant from the infusion pump 28 into the blood. The sensing units 12 can also be used to detect sterilization fluids like formaldehyde, solvents, and other cleaning solutions and chemicals placed in the system 10 prior to use. If not entirely removed, these cleaning solutions can be potentially injected into the patient 14 causing injury or death. The ability to accurately measure density with the sensing units 12 also enables the detection of air bubbles and estimation of their volume.

In view of the above, the sensing units 12 of this invention are able to supplement and/or replace many of the sensors previously required by dialysis treatment systems. As replacements for traditional sensing devices in a dialysis treatment system, sensing units 12 of this invention are shown in the individual lines from the water 30 and dialysate concentrate 32 and the line carrying the resulting dialysate solution, thereby taking the place of conductivity and temperature sensors typically used to monitor the dialysate solution before being introduced into the dialyzer 22. Because of its density-sensing capability, the sensing unit 12 shown in the line connecting the air bubble detector 38 to the venous cannula 18 can replace the bubble detector 38. As supplemental sensors capable of improving the safety and efficacy of the dialysis treatment, sensing units 12 are shown placed between the arterial cannula 16 and the blood pump 20, immediately downstream of the drip chamber 24 and in the line downstream of where the anticoagulant enters the blood stream before being introduced into the dialyzer 22, in the outlet line from the dialyzer 22, in a discharge line connected to the line between the dialyzer 22 and the bubble detector 38, and between the bubble detector 38 and the venous cannula 18. These installations are discussed in more detail below.

Figure 2:
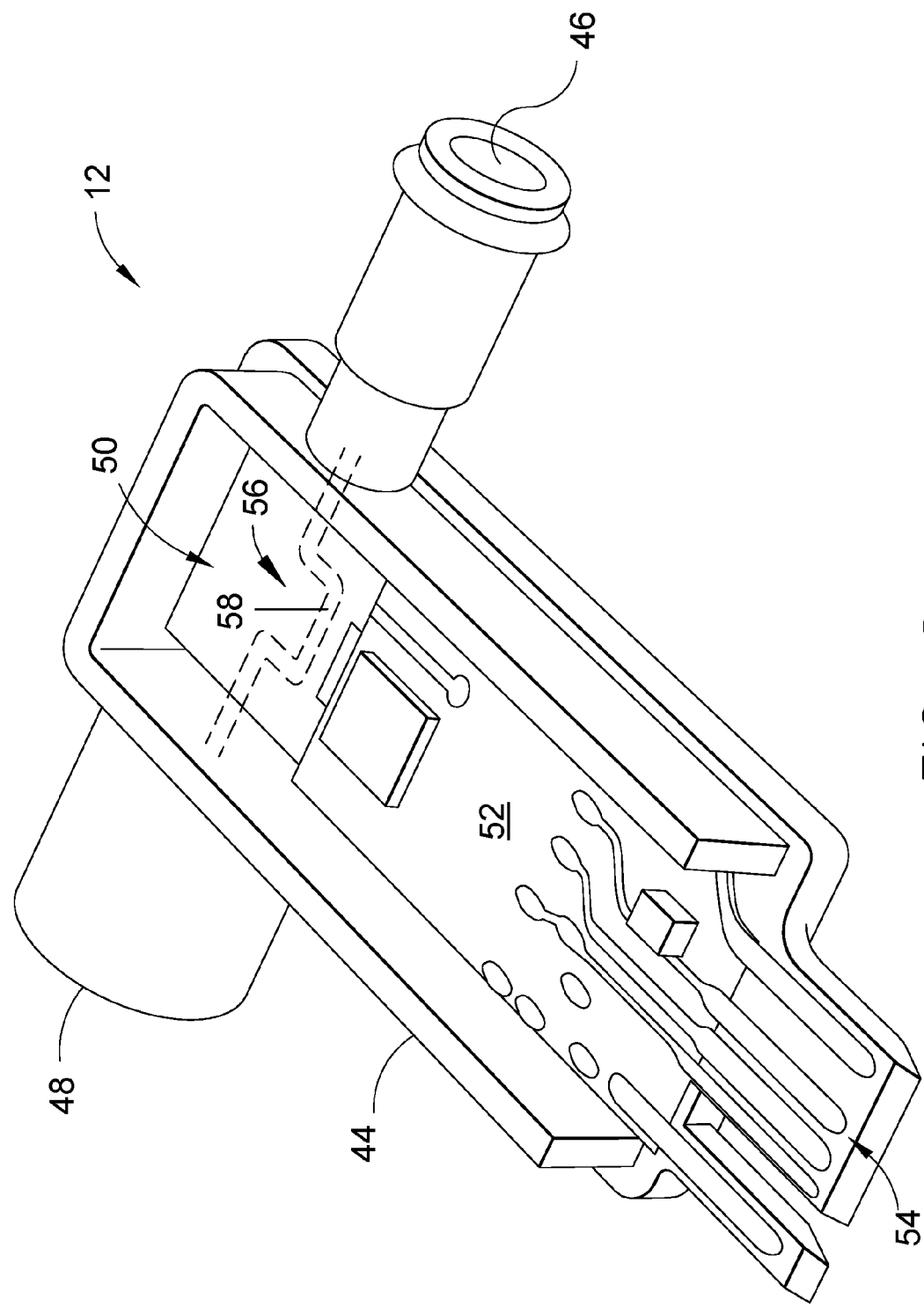
FIG. 2 is a perspective view of a sensing unit for use in the treatment system of FIG. 1.

A suitable configuration for a sensing unit 12 for this invention is depicted in FIG. 2. The unit 12 is shown as comprising a housing 44 adapted for inline installation, though other configurations are also possible and within the scope of this invention. The housing 44 is formed to have a fluid inlet 46 and outlet 48, both of which can be adapted for a fluidic connection through such fittings as a Luer, threaded, compression, barbed, lock or other type of fitting. The housing 44 contains a sensor 50 and electronic circuitry 52 located and enclosed within a cavity defined within the housing 44 and closable with a cover (not shown). The sensor 50 is the structure through which the fluid being sensed flows and provides a measurable response to the density and preferably the flow rate of the fluid. The circuitry 52 is preferably configured to communicate with and control the sensor 50 and output information regarding the operation of the sensing unit 12. The unit 12 further includes an electrical connector 54 by which the circuitry 52 can be coupled to a control unit 80 (FIG. 1) such as a computer or another suitable electronic device capable of controlling and receiving signals from the sensing unit 12. Such a control unit may be hard-wired to the sensing unit 12 with the connector 54, or the connector 54 can be replaced with a wireless communication device of a type known in the art, such as an IR, RF, optical, magnetic, etc. Power for the sensor 50 and circuitry 52 can be provided with a battery (not shown) within the housing 44, delivered through a cable connected via the connector 54, or delivered telemetrically using known tele-powering techniques.

Figure 3:
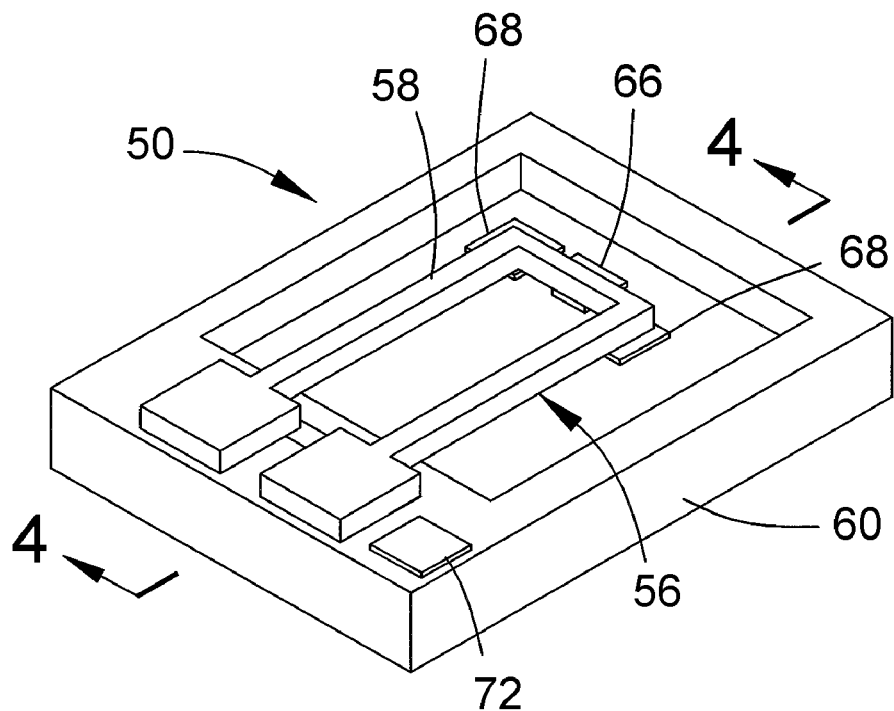
FIGS. 3 and 4 are perspective and cross-sectional views, respectively, of a Coriolis-type mass flow rate sensor suitable for use in the sensing unit of FIG. 2.
Figure 4:
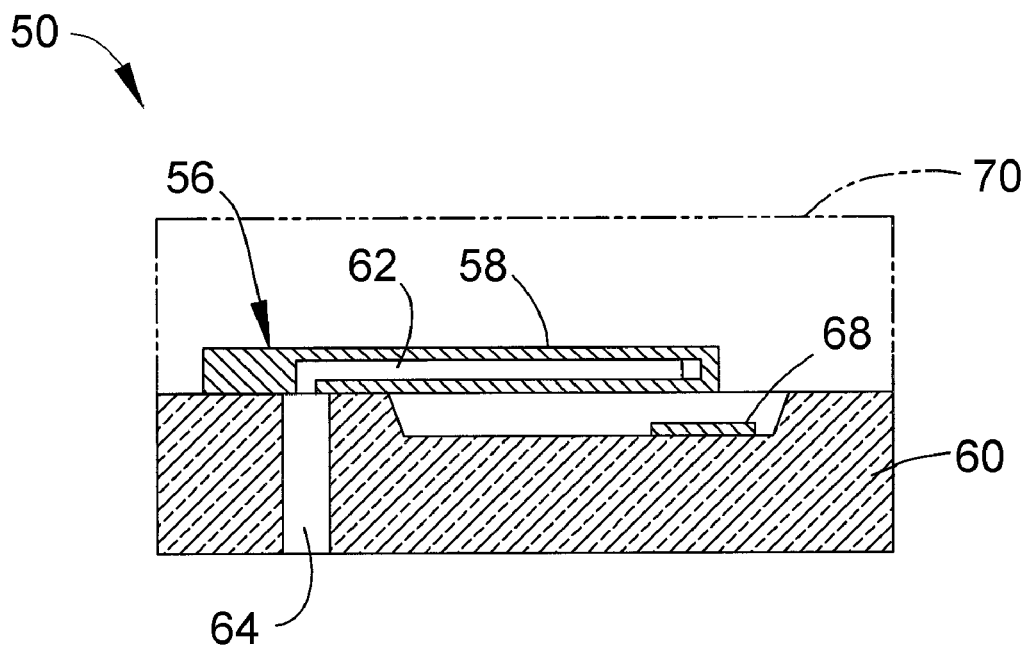

The sensor 50 is represented as comprising a tube 56 that serves as a conduit through which the fluid flows as it flows between the inlet 46 and outlet 48 of the housing 44. In a preferred embodiment of the invention, the sensor 50 and its tube 56 are part of a Coriolis mass flow sensor. FIGS. 3 and 4 depict a preferred Coriolis mass flow sensor 50 taught in commonly-assigned U.S. Pat. No. 6,477,901 to Tadigadapa et al., whose discussion of the construction and operation of the flow sensor thereof is incorporated herein by reference. In Tadigadapa et al., wafer bonding and silicon etching techniques are used to micromachine the tube 56 and its freestanding portion 58, which is suspended over a silicon substrate 60. The freestanding portion 58 of the tube 56 is vibrated at resonance such that, as fluid flows through an internal passage 62 within the tube 56, the freestanding portion 58 twists under the influence of the Coriolis effect. As explained in Tadigadapa et al., the degree to which the freestanding portion 58 twists (deflects) when vibrated can be correlated to the mass flow rate of the fluid flowing through the tube 56 on the basis of the change in the amplitude of a secondary resonant vibration mode. The density of the fluid is proportional to the natural frequency of the fluid-filled vibrating portion 58, such that controlling the vibration of the portion 58 to maintain a frequency at or near its resonant frequency will result in the vibration frequency changing if the density of the fluid flowing through the tube 56 changes. As depicted in FIGS. 2 and 3, the freestanding portion 58 is preferably U-shaped, though other shapes—both simpler and more complex—are within the scope of this invention.

As known in the art, micromachining techniques a capable of forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. Accordingly, suitable materials for the tube 56 include glass (e.g., quartz and Pyrex), ceramic, metal or a semiconductor, including micromachined silicon, germanium, Si/Ge and GaAs. The substrate 60, tube 56, and freestanding portion 58 of the tube 56 are micromachined so that the passage 62 connects ports 64 (one of which is shown) located on the lower surface of the substrate 60. As previously noted, micromachining technologies are preferably employed to fabricate the tube 56, enabling the size of the tube 56 and its freestanding portion 58 and passage 62 to be extremely small, such as lengths of about 0.5 mm and cross-sectional areas of about 100 square micrometers, with the result that the sensor 50 is capable of processing very small quantities of fluid.

The resonant frequency of the freestanding tube portion 58 is determined in part by its mechanical design (shape, size, construction and materials). Suitable frequencies are in the range of 1 kHz to over 100 kHz, depending on the particular fluid being analyzed. Under most circumstances, frequencies above 10 kHz, including ultrasonic frequencies (those in excess of 20 kHz), will be preferred. The amplitude of vibration is preferably adjusted through means used to vibrate the tube portion 58. For this purpose, FIG. 3 shows an electrode 66 located beneath the freestanding portion 58 on the surface of the substrate 60. In the embodiment shown, the tube 56 serves as an electrode (e.g., is formed of doped silicon) that is capacitively coupled to the electrode 66, enabling the electrode 66 to electrostatically drive the freestanding portion 58. However, it is foreseeable that the tube 56 could be formed of a nonconductive material, requiring a separate electrode formed on the freestanding portion 58 opposite the electrode 66 for vibrating the freestanding portion 58 electrostatically. Furthermore, the freestanding portion 58 could be driven capacitively, piezoelectrically, piezoresistively, acoustically, ultrasonically, magnetically, optically, or by another actuation technique. Also shown in FIGS. 3 and 4 are sensing electrodes 68 for providing feedback to enable the vibration frequency and amplitude to be controlled with the circuitry 52 within the sensing unit 12. While capacitive sensing is preferred, the sensing elements 68 could sense the proximity and motion of the freestanding portion 58 in any other suitable manner.

FIG. 4 schematically represents the micromachined tube 56 enclosed by a cap 70 bonded or otherwise attached to the substrate 60. In a preferred embodiment, the bond between the cap 70 and substrate 60 is hermetic, and the resulting enclosure is evacuated to enable the freestanding portion 58 to be driven efficiently at high Q values without damping. A suitable material for the cap 70 is silicon, allowing silicon-to-silicon bonding techniques to be used, though other cap materials and bonding techniques are possible and within the scope of the invention.

The resonating tube flow sensor 50 of Tadigadapa et al. is preferred for use in the sensing units 12 of this invention, though it is foreseeable that other types of flow sensors could be employed. However, particularly advantageous aspects of the resonating tube sensor of Tadigadapa et al. include its very small size and its ability to precisely measure extremely small amounts of fluids, in contrast to prior art Coriolis-type flow sensors. Furthermore, the preferred flow sensor can attain flow rate measurement accuracies of under +/-1%, in contrast to other types of infusion pumps whose accuracies can range from about +/-15% for volumetric pumps and +/-3% for syringe pumps. While the high cost and the high flow rate requirements for prior art Coriolis-type flow sensors have restricted their use in the drug delivery arena, the flow sensor of Tadigadapa et al. is able to sense the extremely low flow rates (e.g., less than 1 ml/hr) required by infusion therapy applications, and can be used to sense the flow rates associated with the dialysis treatment system 10 of FIG. 1. Because of its tube configuration, the sensor 50 also has a bidirectional flow capability that enables the sensing unit 12 to detect incorrect flow direction in the system 10. The sensing unit 12 can be used in a similar manner with peritoneal dialysis and other forms of patient treatment for renal failure and other renal applications, and for a variety of artificial organs and filtration treatments for the kidneys, lungs and liver. For example, an additional sensing unit 12 is shown in FIG. 1 as being employed with a urinary catheter 17 to indicate the specific gravity and concentration of the patient's urine, enabling the patient's health and renal activity to be closely monitored. In this manner, the output of the sensor 50 can be used to indicate a need for further medical treatment, including dialysis. The sensing unit 12 can be mounted in-line as part of the urinary catheter 17, or used to analyze samples drawn from the catheter 17.

In order to provide the temperature-sensing capability desired for the sensing unit 12, the sensor 50 is shown in FIG. 3 as including an on-chip thin film temperature sensor 72, such as a resistance temperature detector (RTD), in close proximity to the resonating tube 56. The temperature sensor 72 is shown integrated on to the same substrate 60 as the tube 56 to provide an accurate fluid temperature output, which in addition to providing useful temperature data also enables temperature to be factored into the fluid density measured by the sensor 50. Alternatively, a temperature sensing capability can be achieved by fabricating a second cantilevered tube on the substrate 60. According to commonly-assigned U.S. Pat. No. 6,647,778 to Sparks, vibrating the cantilevered tube at resonance enables the tube to measure the temperature of the fluid flowing therethrough on the basis that the Young's and shear modulus of the materials used to form the tube change with temperature, causing the resonant frequency of the tube to detectably shift with temperature.

From the above, it can be appreciated that sensing units 12 equipped with the sensor 50 and a temperature-sensing capability (such as with the sensor 72) can be advantageously employed in the hemodialysis treatment system 10 of FIG. 1 to monitor the blood and the various fluids added to and removed from the blood. In particular, it can be seen that the sensing units 12 shown in the individual lines from the water 30 and dialysate concentrate 32 and the line carrying the resulting dialysate solution to the dialyzer 22 are able to accurately monitor and provide feedback control for the flow and subsequent mixing of the water 30 and concentrate 32 before the resultant dialysate solution is introduced into the dialyzer 22, thereby replacing conductivity and temperature sensors typically used to monitor the dialysate solution.

The density-sensing capability of the sensing unit 12 shown in the line connecting the air bubble detector 38 to the venous cannula 18 can be used to sense the density and temperature of the blood returning to the patient 14, the former of which can be used to sense the chemical concentration of urea, hematocrit, blood cells, water, anticoagulants, etc., as well as the presence of other desired and undesired components in the blood. The preferred sensing unit 12 is also sufficiently sensitive to detect fine air bubbles, as reported in commonly-assigned U.S. patent application Ser. No. 10/248, 839 to Sparks and U.S. patent application Ser. No. 10/708,509 to Sparks et al. As such, this sensing unit 12 can entirely replace the bubble detector 38 represented in FIG. 1.

The sensing units 12 placed adjacent the arterial and venous cannulas 16 and 18 are shown as being connected to an analyzer 42 capable of comparing the flow rates sensed by these sensing units 12, enabling the system 10 to detect blood leakage within the system 10 as well as occlusions. As such, these sensing units 12 can replace the blood leak detector 36 represented as being conventionally placed in the outlet line of the dialyzer 22. Alternatively, FIG. 1 shows a sensing unit 12 placed in the outlet line of the dialyzer 22 to directly sense blood leak rates in the dialysate solution leaving the dialyzer 22 by monitoring the density of the dialysate solution.

The sensing units 12 placed immediately downstream of the drip chamber 24, downstream of the anticoagulant fusion pump 28, and in the line downstream of where the anticoagulant enters the blood stream before entering the dialyzer 22 enables the flow rates of the blood and anticoagulant to be accurately monitored to ensure a proper amount of anticoagulant is present in the blood entering the dialyzer 22. Dose and dose rates can also be calculated based on the flow rate measured with these sensors. As noted previously, this capability is advantageous because the preferred sensor 50 is capable of greater accuracy than conventional infusion pumps.

Finally, FIG. 1 shows a sensing unit 12 placed in a discharge line connected to the line between the dialyzer 22 and the bubble detector 38. A valve 40 is represented as being placed in the discharge line to allow limited quantities of blood to be drawn from the system 10 and analyzed with the sensing unit 12 for the purpose of measuring the density of the blood, with the capability of sensing waste, sterilization fluids, etc., in the blood before being returned to the patient 14.

With the system 10 shown, algorithms relating flow rate, flow direction, fluid density, chemical concentration, and temperature can be developed with each individual sensing unit 12 or inputs from several of these sensing units 12 placed as shown at different points in the dialysis system 10. These algorithms can be developed to provide better control of the treatment that the patient 14 receives than is possible with a single parameter sensor, such as the ultrasonic or optical flow sensors used in the past. The sensing units 12 and their control unit(s) 80 also enable dosage rates of the anticoagulant and dialysate solution to be programmed wirelessly via IR, RF, magnetic, optical, or other communication approach, as can the flow rates and concentrations be monitored to detect malfunctions in the system 10. With an appropriate control interface to the control unit 80, programming can be performed by the physician, care giver, nurse, or pharmacist, such as with a wireless two-way data communication system. In this manner, the dose rate of any additive can be adjusted at any time before or during use and can be recorded for later retrieval and evaluation of the treatment. With the sensing units 12, safety limits can also be programmed into the system 10 to prevent overdose or warn if occlusions, leaks, or an unsafe urea or drug concentration is detected. The control interface can also receive inputs from other sensors integrated into the system 10 to sense bodily responses, such as glucose, urea, hematocrit, oxygen, respiration rate, pulse, and other chemical or physiological responses to the treatment, and then adjust or halt the medication delivery rate if necessary. Along this approach, the sensing unit 12 shown in FIG. 1 as monitoring the density (specific gravity) of the patient's urine can be used to indicate when dialysis is needed and/or control the dialysis treatment, e.g., increase or decrease the flow rate of the dialysate solution, anticoagulant, etc.

In some of the above applications, the sensing unit 12 and its sensor 50 must accommodate the relatively high blood flow rates maintained within the system 10 to avoid clotting. High dialysate flow rates through the dialyzer 22 and its dialysis membrane are also desirable to maximize the removal rate of urea and other wastes. Such higher flow rates can be accommodated by designing and inserting the sensing unit 12 as a bypass unit, in which a fraction of the fluid is drawn through the sensing unit 12. Some of the applications within the system 10 also require only density as the sensed parameter. The sensing unit 12 shown in FIG. 2 and described above can be used for this limited purpose, or other density meters can be used such as meters available from the assignee of the present invention. These sensing units 12 can be used to measure density, specific gravity, or chemical concentration of all the fluid flowing through a line, or used in a by-pass mode to sample a portion of the fluid, or sample small portions of fluid from a line, in which case the sample can be discarded as waste. If the sample does not return to the patient 14, the sensing unit 12 can be a durable, reusable portion of the dialysis system 10. Otherwise, the sensing unit 12 can be manufactured as a disposable unit that can be removed after each use of the system 10. Reusable sensing units 12 can be coupled with a valve to admit small test samples of the fluid of interest, which can then be tested for the presence of sterilization fluid, intentionally added drugs, and/or the chemical concentration of such additives as heparin or another anticoagulant, dialysate concentration, or blood hematocrit/red blood cells. In view of the small size of the preferred sensor 50, only very small sample volumes are required for analysis, typically on the order of nanoliters to milliliters in volume.

While the invention has been described in terms of a preferred embodiment, it is apparent that other forms could be adopted by one skilled in the art. Therefore, the scope of the invention is to be limited only by the following claims.

The invention claimed is:

1. A method of treating blood of a living body to perform hemodialysis on the living body, the method comprising the steps of:
    sensing the density of urine excreted by the living body and in response to the density of the urine withdrawing blood from the living body and causing the blood to flow through a treatment system;
    altering at least the density of the blood through the action of a second fluid as the blood flows through the treatment system;
    sensing at least the density and flow rate of the blood before the density thereof is altered by the second fluid, sensing at least the density and flow rate of the blood after the density thereof is altered by the second fluid, and sensing at least the density and flow rate of the second fluid;
    controlling at least one of the density and flow rate of the second fluid based on the sensed densities and flow rates in response to the density of the urine; and
    returning the blood to the living body.

2. The method according to claim 1, wherein the sensing step senses the concentration of a component of the blood chosen from the group consisting of urea, hematocrit, blood cells, water, and anticoagulant.

3. The method according to claim 1, wherein the control step further comprises controlling the altering step based on the sensed density of the blood.

4. The method according to claim 1, wherein the second fluid is an anticoagulant, the altering step comprises introducing the anticoagulant into the blood, and the sensing step comprises sensing the concentration of the anticoagulant prior to being introduced into the blood.

5. The method according to claim 1, wherein the second fluid is a dialysate solution, the altering step comprises flowing the dialysate solution and the blood through a dialyzer to perform dialysis on the blood, and the sensing step comprises sensing the density and flow rate of the dialysate solution entering the dialyzer.

6. The method according to claim 1, wherein the second fluid is a dialysate solution, the altering step comprises flowing the dialysate solution and the blood through a dialyzer to perform dialysis on the blood, and the sensing step comprises sensing the density and flow rate of the dialysate solution leaving the dialyzer.

7. The method according to claim 6, further comprising the steps of:
   combining water and a dialysate concentrate to form the dialysate solution;
   sensing the flow rate of the water being combined with the dialysate concentrate; and
   sensing the flow rate of the dialysate concentrate combined with the water.

8. The method according to claim 1, wherein the sensing step detects sterilization fluids in the blood.

9. The method according to claim 1, wherein the sensing step detects air bubbles in the blood.

10. The method according to claim 1, further comprising sensing the flow rate of the blood in the system and detecting leakage of blood based on the flow rate.

* * * * *